(12) United States Patent
Kim et al.

(10) Patent No.: US 7,426,031 B2
(45) Date of Patent: Sep. 16, 2008

(54) METHOD AND APPARATUS FOR INSPECTING TARGET DEFECTS ON A WAFER

(75) Inventors: Moon-Kyung Kim, Gyeonggi-do (KR); Chung-Sam Jun, Gyeonggi-do (KR); Yu-Sin Yang, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 226 days.

(21) Appl. No.: 11/461,726

(22) Filed: Aug. 1, 2006

(65) Prior Publication Data
US 2007/0030478 A1    Feb. 8, 2007

(30) Foreign Application Priority Data
Aug. 2, 2005    (KR) .................. 10-2005-0070631

(51) Int. Cl.
*G01B 9/08* (2006.01)
*G01N 21/00* (2006.01)
(52) U.S. Cl. .................................... 356/392; 356/237.2
(58) Field of Classification Search .................. None
See application file for complete search history.

(56) References Cited

U.S. PATENT DOCUMENTS

| 5,146,509 A * | 9/1992 | Hara et al. ................. 382/149 |
| 5,436,464 A * | 7/1995 | Hayano et al. ......... 250/559.01 |
| 5,917,588 A | 6/1999 | Addiego |
| 5,982,921 A * | 11/1999 | Alumot et al. .............. 382/145 |
| 6,940,592 B2 * | 9/2005 | Borden et al. ............... 356/326 |
| 7,307,712 B2 * | 12/2007 | Van Der Werf et al. .. 356/237.2 |
| 2004/0086170 A1 * | 5/2004 | Shishido et al. ............. 382/149 |

FOREIGN PATENT DOCUMENTS

| JP | 2003-090803 | 3/2003 |
| KR | 1995-001979 | 1/1995 |
| KR | 1999-0065674 | 8/1999 |
| KR | 2003-0096478 | 12/2003 |
| KR | 10-2005-0049261 | 5/2005 |

OTHER PUBLICATIONS

English language abstract of Korean Publication No. 2003-0096478.
English language abstract of Japanese Publication No. 2003-090803.

* cited by examiner

*Primary Examiner*—Michael P Stafira
(74) *Attorney, Agent, or Firm*—Marger Johnson & McCollom, P.C.

(57) ABSTRACT

A defect inspecting apparatus includes a first support unit supporting a standard sample having standard defects, a second support unit supporting a wafer having target defects, a light source irradiating an incident light to the standard sample or the wafer, a light receiving part collecting reflection light reflected from the standard sample and the wafer, a detection part detecting the standard defects and the target defects by using the reflection light, a comparing part comparing information obtained using the reflection light reflected from the standard sample with a predetermined standard information of the standard defects to confirm a reliability of a step for detecting the target defects and a determination portion determining whether the step is allowed to be performed or not.

21 Claims, 4 Drawing Sheets

METHOD AND APPARATUS FOR INSPECTING TARGET DEFECTS ON A WAFER

CROSS REFERENCE TO RELATED APPLICATION

This application claims benefit of priority under 35 U.S.C. § 119 from Korean Patent Application No. 2005-70631 filed on Aug. 2, 2005, the disclosure of which is incorporated herein by reference in its entirety.

BACKGROUND

1. Field of the Invention

The present invention relates to methods of inspecting target defects on a wafer and defect inspecting apparatuses for performing the methods. More particularly, the present invention relates to methods of inspecting target defects on a wafer, the method capable of confirming the reliability of an inspection result and precisely inspecting the target defects (e.g., a particle and a scratch) on the wafer in a relatively short time.

2. Description of the Related Art

Generally included in the manufacture of highly integrated semiconductor devices is an inspection process for inspecting defects on a wafer. For example, a particle, a bridge, and/or a collapse may be generated on the wafer while a patterning process is performed on the wafer. In addition, a scratch may be generated on the wafer while a chemical mechanical polishing (CMP) process is performed on the wafer. The defect inspecting process may determine if the defects will have adverse influences on succeeding processes.

The number of defects in a semiconductor device generally increases with increasing semiconductor device density. Hundreds to thousands of defects may typically be present. Thus defect detection becomes increasingly important. However, conventional defect inspecting methods and apparatuses are generally slow. In addition, time and cost required for confirming the reliability of the defect inspection process are high.

Recently, inspecting processes may be performed either by a dark field method or by a bright field method. Both the dark and bright field methods compare images of adjacent dies on the wafer to inspect the defects. One presumption of the dark and bright field methods is that the dies are substantially the same. Thus, the defects may be inspected measuring a difference between the images. That is, if the difference is relatively large, defects may exist.

Figure 1:
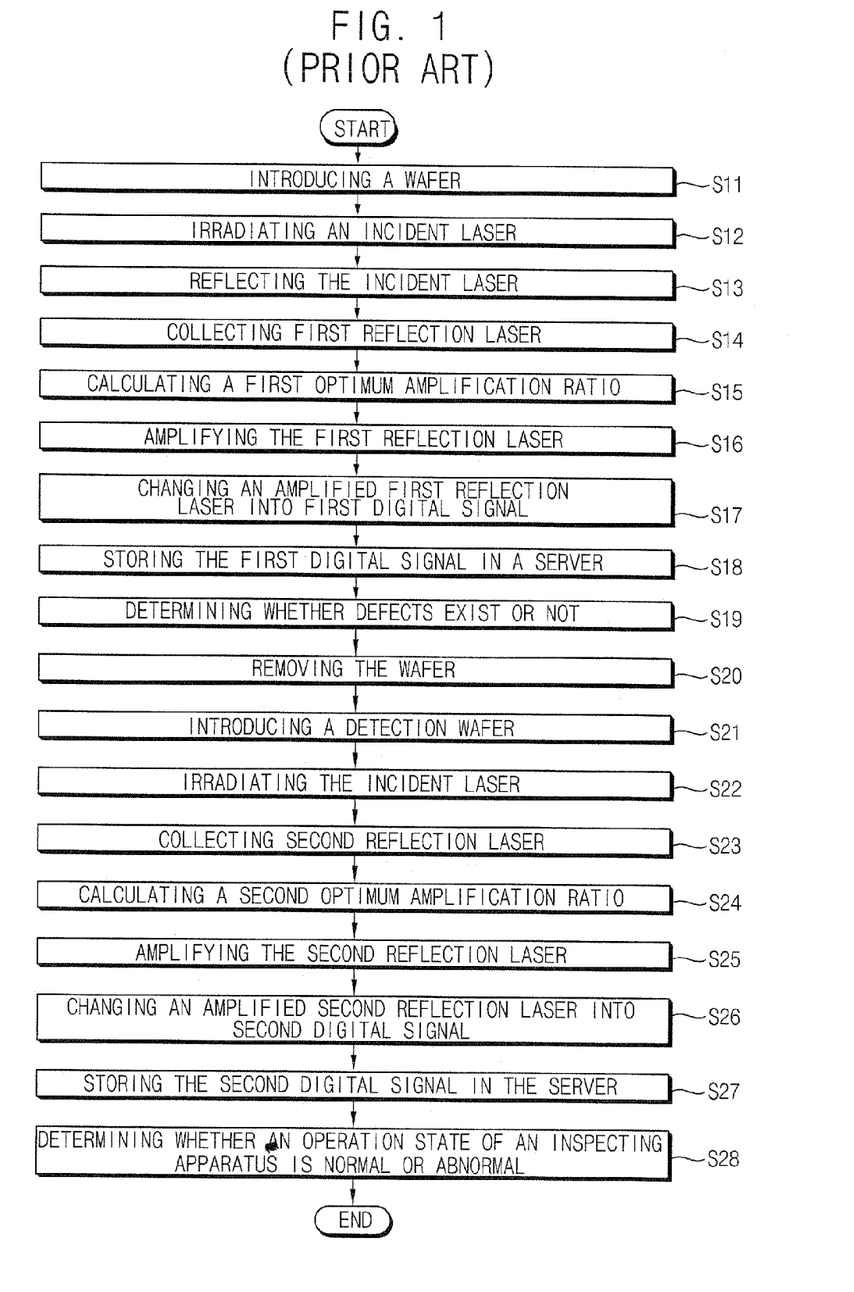
FIG. 1 is a flow chart illustrating a conventional method of inspecting defects on a wafer.

FIG. 1 is a flow chart illustrating a conventional method of inspecting defects on the wafer.

Referring to FIG. 1, the wafer is introduced into a conventional defect inspecting apparatus in step S11. An incident laser beam is incident on the wafer in step S12. The wafer then reflects the incident laser beam, and this reflected laser beam is called a first reflection laser beam, as in step S13. A photo multiplier tube collects the energy of the first reflection laser beam in step S14. The photo multiplier tube determines a first optimum amplification ratio according to an intensity of the first reflection laser beam in step S115. The photo multiplier tube then amplifies the first reflection laser beam signal according to the first optimum amplification ratio so that the first reflection laser beam signal may be changed into an amplified first reflection laser beam signal in step S16. The amplified first reflection laser beam signal may be changed into a first digital signal in step S17. A server stores the first digital signal in step S118. A signal previously obtained from a standard wafer is compared with the first digital signal to determine whether the defects exist on the wafer or not in step S19. In addition, if the defects exist, the number of the defects is measured in step S19. If the number of the defects is over a predetermined limit, an operation of the conventional defect inspecting apparatus may be stopped. The wafer on which the defects exist may then be transferred into a defect review apparatus so that the defects may be precisely reviewed. That is, an examination with the naked eye may be performed on the defects on the basis of information concerning types and positions of the defects. The information may be obtained using the conventional defect inspecting apparatus. For example, shapes of the defects may be measured during the examination. The examination with the naked eye may be performed using a microscope such as a scanning electron microscope (SEM).

After some wafers are inspected, the wafer in the conventional defect inspection apparatus is removed to confirm the inspection reliability of the defects in step S20. A calibration wafer on which standard defects are intentionally generated is introduced into the conventional defect inspection apparatus in step S21. The incident laser beam is irradiated on the calibration wafer in step S22. The calibration wafer may reflect the incident laser beam, which is called a second reflection laser beam. The photo multiplier tube collects energy of the second reflection laser beam in step S23. The photomultiplier tube determines a second optimum amplification ratio according to an intensity of the second reflection laser beam in step S24. The photomultiplier amplifies the second reflection laser beam signal according to the second optimal amplification ratio so that the second reflection laser beam signal may be changed into an amplified second reflection laser signal in step S25. The amplified second reflection laser beam signal is changed into a second digital signal in step S26. The server stores the second digital signal in step S27. Thereafter, a comparison between the second digital signal and the calibration signal that was previously obtained from the calibration wafer is measured to determine whether an operation state of the conventional defect inspecting apparatus is normal or abnormal in step S28. The second digital signal and the calibration signal may be obtained from the same calibration wafer. Thus, if the second digital signal is substantially identical to the calibration signal, the operation state of the conventional defect inspecting apparatus is determined to be normal. However, if the second digital signal is substantially different from the calibration signal, the operation state of the conventional defect inspecting apparatus is determined to be abnormal. As a result, the accuracy of an inspection of the defects may be measured.

For example, a conventional method of inspecting defects is disclosed in U.S. Pat. No. 5,917,588 assigned to KLA-Tencor Corp. In the conventional method, an automated specimen inspection system is used for distinguishing feature or anomalies under either bright field or dark field illumination.

In the conventional method of inspecting the defects, a step for confirming the reliability of an inspection of the defects is performed periodically. Thus, it is possible to rapidly cope with mechanical troubles of the conventional defect inspecting apparatus. Thus, cost increase and time loss may be reduced. However, if the calibration wafer is introduced into the conventional defect inspecting apparatus in the middle of a defect inspection process, some problems may occur. For example, if the calibration wafer is manually introduced into the conventional defect inspecting apparatus or manually removed from the conventional defect inspecting apparatus, the conventional defect inspecting apparatus may be damaged. In addition, because data is manually analyzed, an accuracy of an analysis may be inadequate. Furthermore, a time required for determining whether the operation state of the conventional defect inspecting apparatus is normal or abnormal may be long.

SUMMARY

Some embodiments provide methods and apparatuses of precisely inspecting target defects on a wafer in a relatively short time.

In accordance with some embodiments, methods of inspecting target defects on a wafer include introducing the wafer into a defect inspecting apparatus. A first step is performed to obtain first information concerning standard defects on a standard sample adjacent to the wafer. The first information is compared with predetermined standard information to determine whether an operation state of the defect inspecting apparatus is normal or abnormal. The predetermined standard information is previously obtained by a preliminary step. Whether a second step for inspecting the target defects on the wafer is allowed to be performed or not is determined according to the operation state that is determined by comparing the first information with the predetermined standard information.

In accordance with some embodiments, a defect inspecting apparatus includes a first support unit, a second support unit, a light source, a light receiving part, a detection part, a comparing part and a determination portion. The first support unit supports a standard sample. The second support unit supports a wafer. The second support unit is adjacent to the first support unit. The light source irradiates an incident light onto either the standard sample or the wafer. The light receiving part collects first reflection light and second reflection light reflected from the standard sample and the wafer, respectively. The detection part detects standard defects on the standard sample and target defects on the wafer by using the first reflection light and the second reflection light, respectively. The comparing part compares first information and a standard information to confirm a reliability of a target defect inspecting step for detecting the target defects on the wafer. Here, the first information concerns the standard defects. The first information is obtained using the first reflection light. In addition, the standard information is previously obtained from the standard defects on the standard sample. The determination portion determines whether the target defect inspecting step is allowed to be perform or not.

According to some embodiments, a standard sample is installed inside a defect inspecting apparatus so that an operation state of the defect inspecting apparatus may be rapidly and efficiently confirmed. Thus, target defects on a wafer may be efficiently inspected so that a reliability of a defect inspecting process using the defect inspecting apparatus may increase.

BRIEF DESCRIPTION OF THE DRAWINGS

The above and other advantages of the present invention will become readily apparent by reference to the following detailed description when considered in conjunction with the accompanying drawings in which.

DESCRIPTION OF THE EMBODIMENTS

Embodiments will be described with reference to the accompanying drawings. The present invention may, however, be embodied in many different forms and should not be construed as limited to the embodiments set forth herein. Rather, the embodiments are provided so that disclosure of the present invention will be thorough and complete, and will fully convey the scope of the present invention to those skilled in the art. The principles and features of this invention may be employed in varied and numerous embodiments without departing from the scope of the present invention. In the drawings, the size and relative sizes of layers and regions may be exaggerated for clarity. The drawings are not to scale. Like reference numerals designate like elements throughout the drawings.

It will also be understood that when an element or layer is referred to as being "on" another element or layer, the element or layer may be directly on the other element or layer or intervening elements or layers may be present. As used herein, the term "and/or" may include any and all combinations of one or more of the associated listed items.

It will also be understood that, although the terms first, second, etc. may be used herein to describe various elements, components, regions and/or sections. These elements, components, regions and/or sections should not be limited by these terms. These terms may be used to distinguish one element, component, region and/or section from another element, component, region and/or section. For example, a first element, component, region and/or section discussed below could be termed a second element, component, region and/or section without departing from the teachings of the present invention.

The terminology used herein is for the purpose of describing particular embodiments only and is not intended to limit of the invention. As used herein, the singular terms "a," "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence and/or addition of one or more other features, integers, steps, operations, elements, components, and/or groups thereof.

Unless otherwise defined, all terms (including technical and scientific terms) used herein may have the same meaning as what is commonly understood by one of ordinary skill in the art.

It will be further understood that terms, such as those defined in commonly used dictionaries, should be interpreted as having a meaning that is consistent with their meaning in the context of the relevant art and will not be interpreted in an idealized and/or overly formal sense unless expressly so defined herein.

Figure 2:
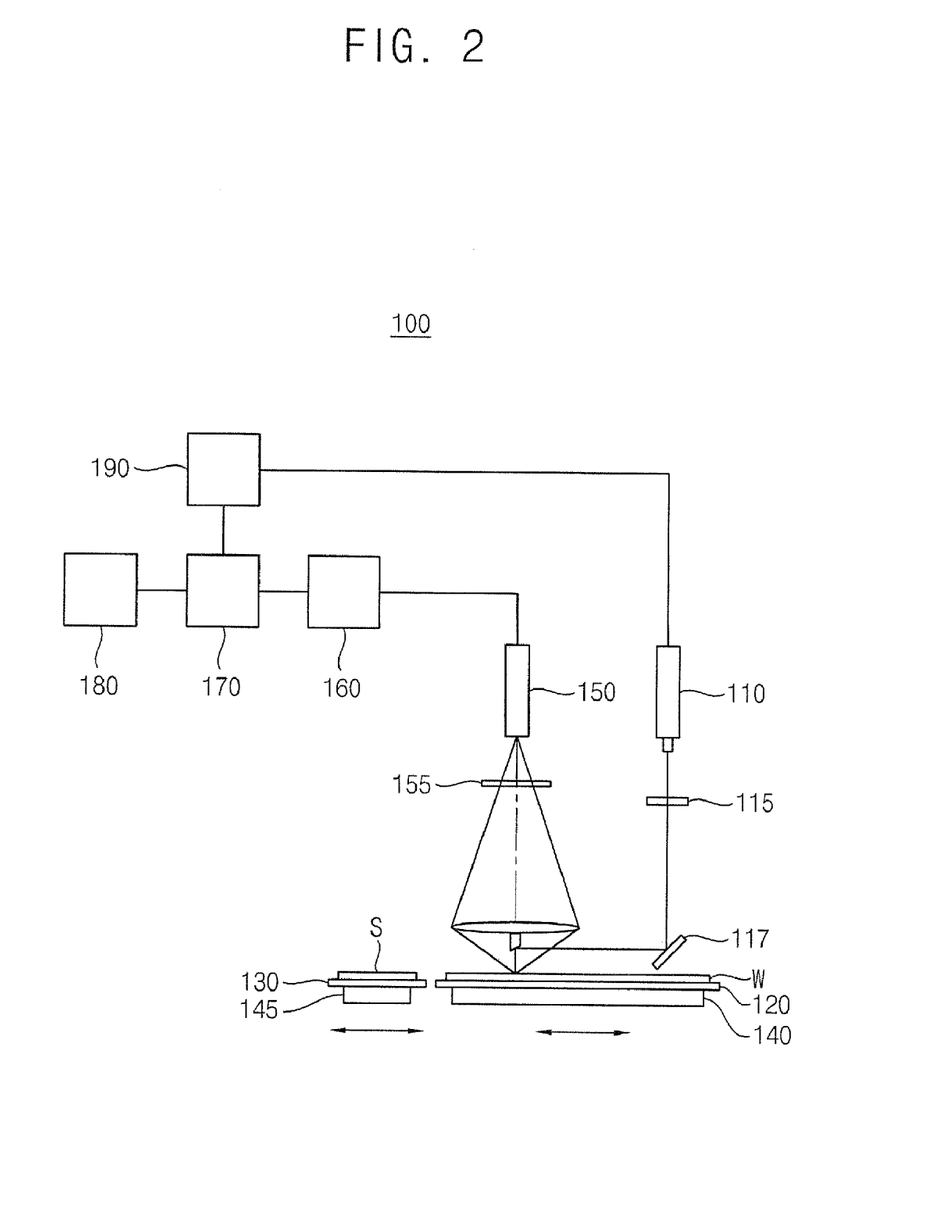
FIG. 2 is a cross-sectional view illustrating a defect inspecting apparatus in accordance with some embodiments.
Figure 3:
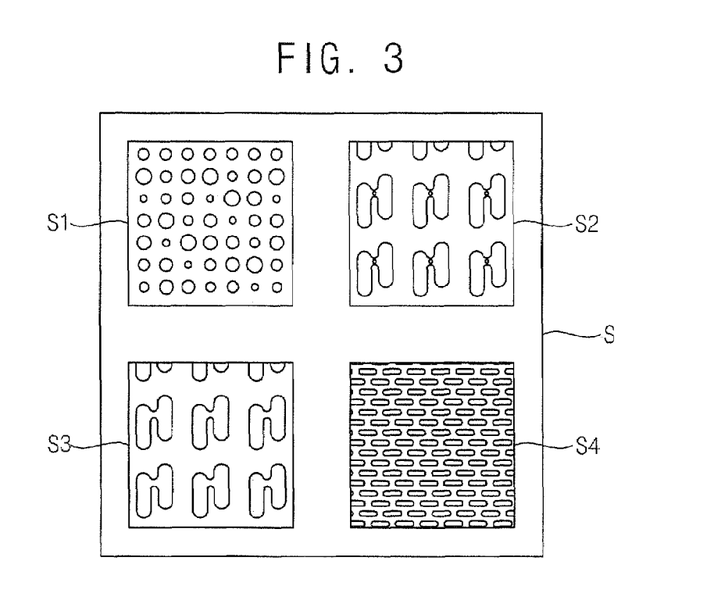
FIG. 3 is a plan view illustrating the standard sample shown in FIG. 2.

FIG. 2 is a cross-sectional view illustrating a defect inspecting apparatus in accordance with some embodiments. FIG. 3 is a plan view illustrating the standard sample shown in FIG. 2.

Referring to FIGS. 2 and 3, a defect inspecting apparatus 100 includes a light source 110, a first support unit 130, a second support unit 120, a first drive unit 145, a second drive unit 140, a light receiving part 150, a detection part 160, a comparing part 170, a memory part 180 and a control part 190.

The light source 110 generates light incident onto a standard sample S on either the first support unit 130 or a wafer W on the second support unit 120. The incident light may include a WLR ray having a wavelength of about 500 nm to about 600 nm, a WL ray having a wavelength of about 365 nm to about 600 nm, a broadband ultraviolet (BBUV) ray having a wavelength of about 350 nm to about 450 nm, an SUV ray having a wavelength of about 365 nm, a deep ultraviolet ray having a wavelength of about 100 nm to about 300 nm, or an extreme ultraviolet (EUV) ray having a wavelength of below about 100 nm. The incident light may be incident onto either the wafer W or the standard sample S through a first optical member 115.

The first optical member 115 may improve optical characteristics of the incident light. In addition, the first optical member 115 may filter the incident light so that the incident light may have a predetermined wavelength. Thus the first optical member 115 may include lenses, spectral filters, or both. The first optical member 115 may include a polarization plate or an aperture. In addition, an optical path changing member 117 may be located on an optical path of the incident light to change the optical path of the incident light. The optical path changing member 117 may include a mirror or a prism.

The incident light may be incident on either the wafer W or the standard sample S at various incident angles. The incident angles may range from about 10° to about 90°. For example, the incident angle is about 90°.

As mentioned above, the incident light may be incident onto either the standard sample S or the wafer W. Particularly, the incident light may be incident onto the standard sample S in a first step. On the other hand, the incident light may be incident onto the wafer W in a second step. If the incident light is incident onto the wafer W in the second step, target defects on the wafer W may be inspected. On the other hand, if the incident light is incident onto the standard sample S in the first step, reliability of the second step may be confirmed. So that the incident light may be selectively incident onto either the wafer W or the standard sample S, the optical path of the incident light may vary. As one alternative, the incident light may be separated into a first beam and a second beam. The first beam and the second beam may then be incident onto the standard sample S and the wafer W, respectively. As another alternative, the light source 110 includes first and second portions generating first and second incident lights, respectively. The first incident light and the second incident light may then be incident onto the standard sample S and the wafer W, respectively. As still another alternative, positions of the standard sample S and the wafer W may vary so that either the standard sample S or the wafer W may be located on the optical path of the incident light.

A combination of optical elements may be used to steer the incident light vertically, or any other angle, onto the surface of the wafer or standard sample, as illustrated in FIG. 2. For example, a series of mirrors may be used to steer the incident light vertical onto the wafer. Light reflecting vertically from the wafer may follow a path different from that of the incident light by using a combination of beam splitters and/or lenses, for example.

Hereinafter, description will be limited to the embodiments where the positions of the standard sample S and the wafer W vary. However, the following embodiments are illustrative and are not to be construed as a limitation of the present invention.

Fine structures required for manufacturing a memory device or a non-memory device may be repeatedly or non-repeatedly formed on the wafer W. If A memory chip, for example, may include a die having about 70% to about 80% of first fine structures that are repeatedly formed and about 20% to about 30% of second fine structures that are non-repeatedly formed. An example of the first fine structure includes a cell. An example of the second fine structure includes a peripheral portion, a sense amplifier (S/A), or a sub-word divider (SWD). For a non-memory chip or a system on chip (SOC), at least one of a static random access memory (SRAM), a dynamic random access memory (DRAM), a logic device, and a flash memory may be non-repeatedly formed. Here, cells may be repeatedly formed in the SRAM, the DRAM, and the flash memory. That is, both the memory chip and the non-memory chip may have first regions where the first fine structures are repeatedly formed and second regions where the second fine structure are non-repeatedly formed. The first and second fine structures formed on the first and second regions, respectively, may be spaced apart form each other by various intervals.

If the fine structures are formed on the wafer W, the target defects may be generated on the wafer W. An example of target defects includes a particle, a scratch, a void, a bridge, or a sink. If the level of the target defects is over a predetermined level, the target defects may cause an operation error of a semiconductor device. In this case it may be necessary to inspect the target defects. The inspection may be performed while the wafer W is supported on the second support unit 120 of the defect inspecting apparatus 100.

For calibration purposes, standard defects are intentionally generated on the standard sample S. The standard sample S is used to determine whether the defect inspecting apparatus 100 is operating normally or not. The standard sample S may include first, second, third, and fourth standard sample units S1, S2, S3, and S4. First, second, third and fourth standard defects are generated on the first, second, third and fourth sample units S1, S2, S3, and S4, respectively. The first, second, third, and fourth standard defects are substantially different from one another. Each of the first, second, third, and fourth standard sample units S1, S2, S3, and S4 has a size substantially the same as that of the die or a chip formed on the wafer W. The first, second, third, and fourth standard sample units S1, S2, S3, and S4 may be regularly arranged on the standard sample S. The first, second, third, and fourth standard defects may be defects of interest (DOI). For example, the first standard defects on the first standard sample unit S1 may be polystyrene sphere latex (PSL) particles having various sizes. The second standard defects on the second standard sample units S2 may be voids having various sizes. The third standard defects on the third sample units S3 may be bridges having various sizes. The fourth standard defects on the fourth standard sample units S4 may be sinks having various sizes. The first, second, third, and fourth standard sample units S1, S2, S3, and S4 may be selectively formed on the standard sample S. In addition, types of standard sample units formed on the standard sample may be changed.

The standard defects of the standard sample S may be previously inspected in a preliminary step. Thereafter, the standard sample S is set onto the second support unit 130 for the first step. Because the standard defects of the standard sample S are already inspected in the preliminary step, standard information concerning the standard defects on the standard sample S may be obtained before the standard sample S is set onto the second support unit 130 for the first step. The standard information may include a contrast of light reflected from the standard defects in the preliminary step, a polarity of the light, a brightness of the light, a statistical value of the light, a background data of the light, a signal intensity of the light, a noise of the light, a signal to noise (S/N) of the light, the number of the standard defects and/or kinds of standard defects.

The preliminary step may be substantially the same as the first step utilizing the defect inspecting apparatus 100 for inspecting the standard defects on the standard sample S. That is, the preliminary step may also utilize the defect inspecting apparatus 100 to obtain the standard information. Alternatively, the standard information may be obtained using an optical inspection device. An example of the optical inspection device may include a microscope or a scanning electron microscope.

As described above, the standard information may be precisely obtained in the preliminary step. The standard information may be stored in the memory part 180. Here, the standard information may be stored in the memory part 180 as a chart divided into first, second, third, and fourth portions concerning the first, second, third, and fourth units S1, S2, S3, and S4, respectively. The standard information stored in the memory part 180 may be used to determine if the defect inspecting apparatus 100 is operating normally or not. That is, the standard information may be used to confirm the reliability of the second step of inspecting the target defects on the wafer W. The standard sample S may be supported on the first support unit 130 while the first step is performed. The wafer W may be supported on the second support unit 120 while the second step is performed.

The first support unit 130 may be adjacent to the second support unit 120. Upper faces of the first and second support units 130 and 120 may be substantially coplanar so that the standard sample S and the wafer W may be inspected under substantially the same conditions. The first drive unit 145 is installed at the first support unit 130 to horizontally move the standard sample S. The second drive unit 140 is installed at the second support unit 120 to horizontally move the wafer W.

The first and second drive units 145 and 140 move the first and second support units 130 and 120, respectively, so that the incident light generated by the light source 110 may be selectively incident onto either the standard sample S or the wafer W. In order to inspect target defects on the wafer W, the second support unit 120 may be dispersed in the optical path of the incident light. On the other hand, in order to confirm the reliability of the second step, the first support unit 130 may be disposed in the optical path of the incident light instead of the second support unit 120. That is, the incident light may be selectively incident onto either the standard sample S or the wafer W only by varying the positions of the first and second support units 130 and 120 without varying the light source 110. In addition, the first and second drive units 145 and 140 may move at substantially constant speeds so that the incident light may be selectively incident onto either the standard sample S or the wafer W in a scanning manner. The first and second support units 130 and 120 may be integral.

Figure 4:
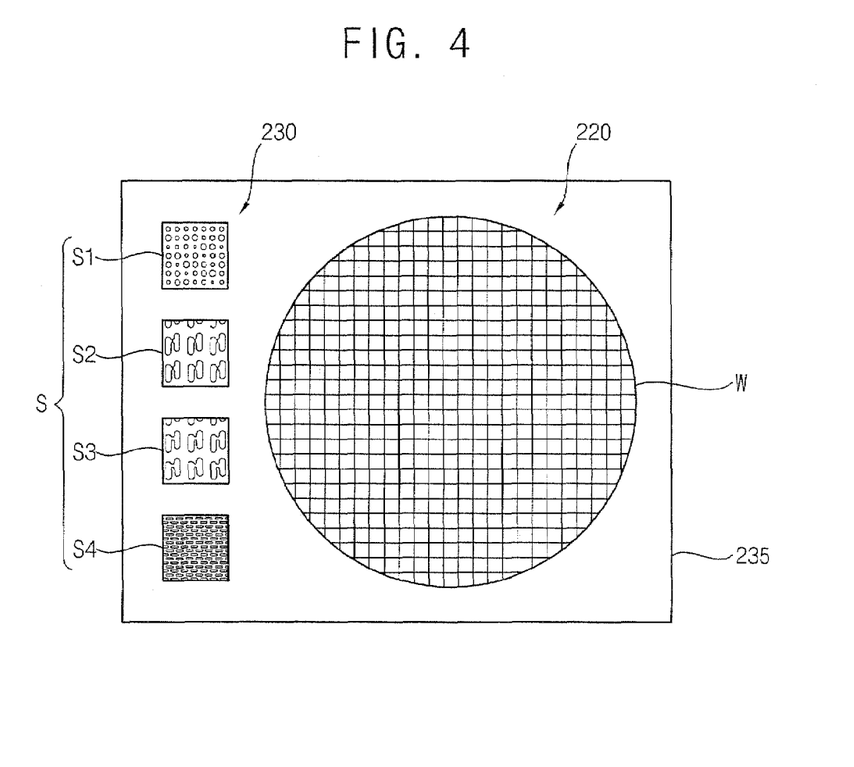
FIG. 4 is a plan view illustrating first and second support units in accordance with some embodiments.

FIG. 4 is a plan view illustrating first and second support units in accordance with some embodiments.

First and second support units 230 and 220 are formed on a stage 235. The stage 235 may support and move the standard sample S and the wafer W. The stage 235 may be in the optical path of the incident light generated from the light source 110. The stage 235 may be divided into a first support unit 230 on which the standard sample S is supported and a second support unit 220 on which the wafer W is supported.

The second support unit 220 may be located at a central portion of the stage 235. The first support unit 230 may be located around the second support unit 220. Upper faces of the first and second support units 230 and 220 may be substantially coplanar so that the standard sample S and the wafer W may be inspected under substantially the same conditions.

The standard sample S is detachably fixed to the first support unit 230. Thus, the standard sample S fixed to the first support unit 230 may be easily exchanged with another sample. The standard sample S may include the first, second, third, and fourth standard sample units S1, S2, S3, and S4.

A drive unit (not shown) may be installed at a lower portion of the stage 235 to provide the stage 235 with a horizontal driving force. The stage 235 may drive the first support unit 230 or the second support unit 220 in the optical path of the incident light so that it may be selectively incident onto either the standard sample S or the wafer W. The stage 235 may utilize coordinate information to precisely place the first support unit 230 or the second support unit 220 in the optical path of the incident light. In addition, the stage 235 may move at substantially constant speed so that the incident light may be selectively incident onto either the wafer W or the standard sample S in a scanning manner.

Referring again to FIGS. 2 and 3, the incident light incident onto the standard sample S or the wafer W may be reflected by the standard sample S or the wafer W. Incident light reflected from the standard sample S will include information concerning the standard defects on the standard sample S. For example, information regarding the standard defects may include shapes and positions of the standard defects. On the other hand, incident light reflected by the wafer W may include information concerning the target defects on the wafer W. For example, information may concern shapes and positions of the target defects on the wafer W. In addition, other information may concern shapes and positions of the fine structures. The light receiving part 150 may collect the reflected light.

The light receiving part 150 may generate a reflection signal in response to detecting light reflected from the wafer or standard sample. Particularly, first and second reflection signals are obtained from the first and second reflected light, respectively. The light receiving part 150 may extend in a vertical direction. In addition, the light receiving part 150 may be substantially in parallel with the light source 110. Thus, the light source 110 may vertically emit the incident light. The reflected light may be vertically incident into the light receiving part 150.

The light receiving part 150 may generate a voltage corresponding to the reflected light. The light receiving part 150 may include a photo multiplier tube (PMT), a photo diode, a photo transistor, a photoelectric tube and etc. A second optical member 155 may be located in front of the light receiving part 150 so that spurious light in the reflected light may be removed. An example of the second optical member 155 may include a polarization plate or an aperture.

After the light receiving part 150 collects the reflected light, the light receiving part 150 may amplify the signal resulting from the reflected light. Thus, the reflected light may be changed into an amplified reflected light signal. Because an intensity of the reflected light collected by the light receiving part 150 is substantially small, it is usually required to amplify the reflected light. An amplification ratio may be controlled by an intensity of voltage applied to the light receiving part 150. The light receiving part 150 may generate photoelectrons corresponding to the amplified reflected light so that a photocurrent may be generated.

If the standard sample S or the wafer W is scanned with the incident light, the incident light may be continuously reflected by the wafer W or the standard sample S. Thus, the light receiving part 150 continuously collects the reflected light to continuously generate the photocurrent. An intensity of the photocurrent may be substantially in proportional to an intensity of the reflected light. Thus, a variation of the intensity of the reflective light may be measured by measuring a variation of an intensity of the photocurrent. The photocurrent generated from the light receiving part 150 may correspond to the reflected signal concerning the intensity of the reflected light. The intensity of the reflected light may be expressed using an intensity of the incident light.

A reflection profile of the second reflected light reflected from the wafer W may vary with characteristics of a layer on the wafer W, characteristics of the fine structures on the layer and the target defects on the layer or the fine structures. If the wafer W has a flat surface that is free of defects, the incident light incident onto the wafer W at an incident angle may be changed into the second reflected light having a reflection angle substantially the same as the incident angle. However, if fine particles are on the wafer W, the incident light incident onto the wafer W may be partially scattered by the fine particles. If a shape of the fine particle is a substantial sphere, the intensity of the second reflected light may be expressed as Equation 1 using the intensity of the incident light.

Equation 1

$$I_s = \frac{8\pi^4 a^6}{\lambda^4 R^4} \left| \frac{n^2 - 1}{n^2 + 2} \right|^2 (1 + \cos^2\theta) I_i$$

In Equation 1, "$I_s$" is the intensity of the second reflected light. "$I_i$" is the intensity of the incident light. "$\lambda$" is a wavelength of the incident light. "n" is a refractive index varying with the fine particle. "R" is a distance between the wafer W and the light receiving part 150. "a" is a diameter of the fine particle. "$\theta$" is the incident angle of the incident light.

Referring to Equation 1, the intensity of the second reflected light may vary with characteristics of the layer on the wafer W, the characteristics of the fine structures on the layer and the target defects on the layer and the fine structures. Thus, the second information concerning the characteristics of the layer, the fine structures and the target defects may be obtained by analyzing the second reflection signal generated from the light receiving part 150.

The detection part 160 analyzes the first and second reflection signal provided from the light receiving part 150 to inspect the standard defects on the standard sample S and the target defects on the wafer W, respectively. The detection part 160 may include a measurement module 165. The measurement module 165 may measure the number of the target defects on the wafer W and the number of the standard defects on the standard sample S.

The measurement module 165 may count the number of peaks of the first and second reflection signals, the peaks varying over a predetermined level, so that the number of the target defects on the wafer W and the number of the standard defects on the standard sample S may be measured. In addition, the measurement module 165 may obtain reflection information relating to the contrast of the reflected light, the polarity of the reflected light, the size of the reflected light, the statistical value of the reflected light, the background data of the reflected light, the signal intensity of the reflected light, the noise of the reflected light and/or the signal to noise S/N of the reflected light from the reflection signal. The defect information may enable the target defects on the wafer W and the standard defects on the standard sample S to be inspected.

As described above, the reliability of the second step performed on the wafer W may be confirmed using the first reflected light reflected from the standard sample S.

The comparing part 170 may compare the first information provided from the detection part 160 with the standard information memorized in the memory part 180 to measure the reliability of the second step. In this case, the standard information is previously obtained by precisely inspecting the standard sample S. In addition, reliability of the standard information is substantially about 100%.

The comparing part 170 may determine whether the first information obtained using the defect inspecting apparatus 100 is substantially the same as the standard information or not. The comparing part 170 then determines whether the operation state of the defect inspecting apparatus 100 is normal or abnormal.

The comparing part 170 may determine whether the operation state of the defect inspecting apparatus 100 is normal or abnormal in various manners. For example, the comparing part 170 may measure a first size of the standard defect from the first information. The comparing part 170 then compares the first size of the standard defect with a second size of the standard defect. Here, the second size of the standard defect may be obtained from the standard information. The comparing part 170 then calculates a difference between the first and second sizes. Thereafter, the comparing part 170 determines whether the operation state of the defect inspecting apparatus 100 is normal or abnormal with reference to a degree of identity between the first and second sizes. For example, if the second size of the standard defect is less than about 200 nm, an allowable limit of the difference between the first and second sizes may be less than about ±3 nm. If more than about 90% of difference between the first and second sizes is within the allowable limit of the difference, the operation state of the defect inspecting apparatus 100 may be determined to be normal. As one alternative, the comparing part 170 may measure the first number of the standard defects from the first information. The comparing part 170 then compares the first number of the standard defects with the second number of the standard defects. Here, the second number of the standard defects may be obtained from the standard information. The comparing part 170 then calculates a difference between the first number of the standard defects and the second number of the standard defects. Thereafter, the comparing part 170 determines whether the operation state of the defect inspecting apparatus 100 is normal or abnormal with reference to a degree of identity between the first number of the standard defects and the second number of the standard defects. For example, if the second number of the standard defects is about 1,000, an allowable limit of the difference between the first number of the standard defects and the second number of the standard defects may be about ±100. If a difference between the first number of the standard defects and the second number of the standard defects is within the allowable limit of the difference, the defect inspecting apparatus 100 may be determined to be normal.

As another alternative, the comparing part 170 may measure first signal to noise (S/N) from the first information. The comparing part 170 then compares the first signal to noise (S/N) with second signal to noise (S/N). Here, the second signal to noise (S/N) may be obtained from the standard information. The comparing part 170 then calculates a difference between the first signal to noise (S/N) and the second signal to noise (S/N). Thereafter, the comparing part 170 determines whether the operation state of the defect inspecting apparatus 100 is normal or abnormal with reference to a degree of identity between the first signal to noise (S/N) and the second signal to noise (S/N). In this case, the first signal to noise (S/N) and the second signal to noise (S/N) may concern a defect of interest (DOI). As still another alternative, a contrast of the first reflected light, a polarity of the first reflected light, a size of the first reflected light, a statistical value of the first reflected light, a background data of the first reflected light, a signal intensity of the first reflected light, a noise of the first reflected light and/or a signal to noise S/N of the first reflected light may be used to determine whether the operation state of the defect inspecting apparatus 100 is normal or abnormal. The comparing part 170 then provides the control part 190 with the operation state of the defect inspecting apparatus 100.

The control part 190 generally controls steps performed using the defect inspecting apparatus 100. The comparing part 170 may determine whether the second step is allowed to perform or not with reference to the operation state of the defect inspecting apparatus 100. If the operation state of the defect inspecting apparatus 100 is determined to be normal. The control part 190 may allow the defect inspection apparatus 100 to perform the second step on the wafer W. However, if the operation state of the defect inspection apparatus 100 is determined to be abnormal, the control part 190 may temporarily stop the second step performed on the wafer W. The control part 190 then generates warning signal indicating an abnormal operation state of the defect inspecting apparatus 100. In addition, the control part 190 may allow the defect inspecting apparatus 100 to automatically perform the first step by periods. However, the first step may be performed regardless of the control part 190.

The first information and the standard information are obtained from the standard sample S. Thus, if the defect inspection apparatus 100 is normal, the first information may be substantially the same as the standard information. As described above, the operation state of the defect inspecting apparatus 100 may be determined to be normal or abnormal in accordance with a degree of identity between the first information and the standard information. The standard sample S is installed inside the defect inspecting apparatus 100 so that the operation state of the defect inspection apparatus 100 may be efficiently determined to be normal or abnormal. Thus, it is possible to rapidly find and then correct the abnormal state of the defect inspecting apparatus 100. As a result, the reliability of the second step may be improved.

Figure 5:
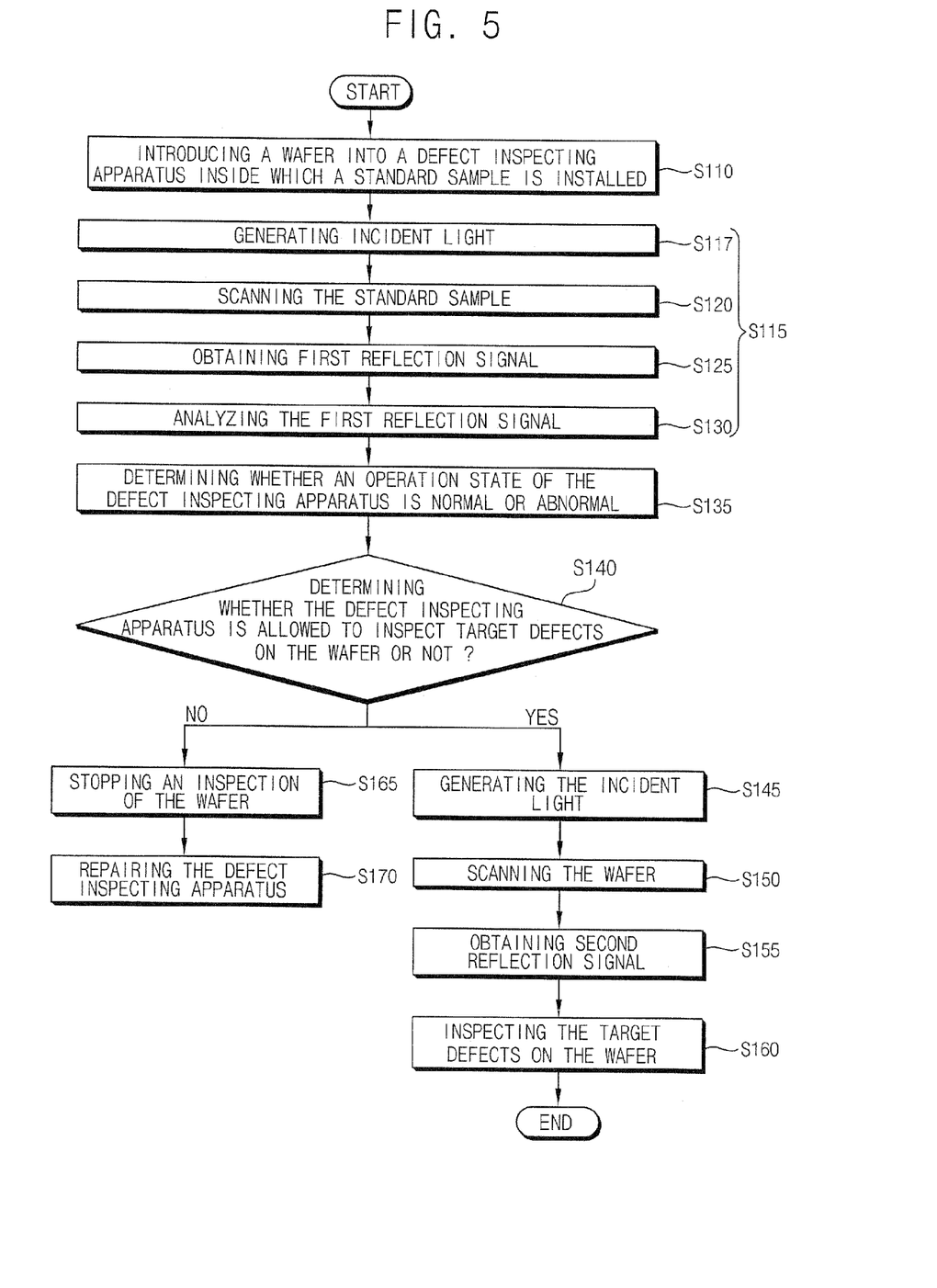
FIG. 5 is a flow chart illustrating methods of inspecting target defects on a wafer in accordance with some embodiments.

FIG. 5 is a flow chart illustrating methods of inspecting target defects on a wafer in accordance with some embodiment of the present invention.

Referring to FIG. 5, a wafer W is introduced into a defect inspecting apparatus 100 inside which a standard sample S is installed in step S110. Standard defects are intentionally generated on the standard sample S. The standard sample S is utilized for determining whether an operation state of the defect inspecting apparatus 100 is normal or abnormal. The standard sample S may include first, second, third and fourth standard sample units S1, S2, S3 and S4 on which first, second, third and fourth standard defects are generated, respectively. The first, second, third and fourth standard defects are substantially different from one another. The first, second, third and fourth standard defects may be defects of interest (DOI). Kinds of sample units on the standard sample S may vary. The kinds of the sample units may vary after the wafer W is introduced into the defect inspecting apparatus 100.

First information concerning the standard defects on the standard sample S may be obtained using the defect inspecting apparatus 100 in step S115. Particularly, incident light is generated from a light source 10 in step S117. The standard sample S is scanned with the incident light in step S120. A first reflected light reflected from the standard sample S is collected so that first reflection signal may be obtained from the first reflected light in step S125. The first reflection signal is analyzed in step S130. Here, an optical path of the incident light may vary so that the standard sample S may be located on the optical path of the incident light. Alternatively, the standard sample S may move so that the standard sample S may be located on the optical path of the incident light. In the present embodiments, the standard sample S is inspected in a dark field inspection method using a scattering of the incident light. Alternatively, the standard sample S may be inspected in a bright field method using a rapid microscope.

The first information is then compared with standard information to determine whether the operation state of the defect inspecting apparatus 100 is normal or abnormal in step S135. Here, the standard information is previously obtained in advance by previously inspecting the standard defects on the standard sample S. The standard information is memorized in a memory part 180. The standard information may concern the number of the standard defects, kinds of standard defects, a signal of light reflected from the standard defects, etc.

The operation state of the defect inspecting apparatus 100 may be determined to be normal or abnormal in various methods. As one example, a size of a first peak point concerning the standard defect on the standard sample S is measured using the first information. Here, the first peak point may be provided from a detection part 160. A difference in size between the first peak point and a second peak point is calculated. Here, the second peak point is provided form the standard information. The operation state of the defect inspecting apparatus 100 may be determined to be normal or abnormal with reference to the difference in size between the first and second peak points. As another example, first signal to noise (S/N) concerning the standard defect on the standard sample is measured using the first information. Here, the fist signal to noise (S/N) may be provided front the detection portion 160. The first signal to noise (S/N) is then compared with second signal to noise (S/N) obtained from the standard information. A difference between the first signal to noise (S/N) and the second signal to noise (S/N) is calculated. Thereafter, the operation state of the defect inspecting apparatus 100 is determined to be normal or abnormal with reference to a degree of identity between the first signal to noise (S/N) and the second signal to noise (S/N). As still another example, a contrast of the first reflected light, a polarity of the first reflected light, a size of the first reflected light, a statistical value of the first reflected light, a background data of the first reflected light, a signal intensity of the first reflected light, a noise of the first reflected light and/or a signal to noise S/N of the first reflected light may be used to determine whether the operation state of the defect inspecting apparatus 100 is normal or abnormal.

Thereafter, whether the defect inspecting apparatus 100 is allowed to inspect target defects on the wafer W or not is determined with reference to the operation state of the defect inspecting apparatus 100 in step S140.

As one example, if a second size of the standard defect, the second size obtained from the standard information, is about 200 nm, an allowable limit of the difference between the second size and a first size that is obtained from the first information may be 13 nm. Here, if more than about 90% of difference between the first and second sizes is within the allowable limit of the difference, the operation state of the defect inspecting apparatus 100 may be determined to be normal. As another example, if more than about 80% of the first signal to noise (S/N) is substantially the same as the second signal to noise (S/N), the operation state of the defect inspecting apparatus 100 may be determined to be normal.

If the operation state of the defect inspecting apparatus 100 is determined to be normal, the target defects on the wafer W in the defect inspecting apparatus 100 are inspected. Particularly, the incident light is generated from the light source 110 in step S145. The wafer W is scanned with the incident light in step S150. A second reflected light reflected from the wafer W is collected so that second reflection signal concerning the second reflected light may be obtained in step S155. The second reflection signal is analyzed to inspect the target defects on the wafer W in step S160. Here, the target defects on the wafer W may be inspected in a manner substantially the same as that employed in inspecting the standard defects on the standard sample S. That is, the incident light scans the wafer W so that the second reflection signal may be obtained. The second reflection signal is analyzed so that the target defects on the wafer W may be inspected in step S160. Here, the optical path of the incident light may vary so that the wafer W may be located on the optical path of the incident light. Alternatively, a position of the wafer W may vary so that the wafer W may be located on the optical path of the incident light.

If the operation state of the defect inspection apparatus is determined to be abnormal, an inspection of the wafer W may be stopped in step S165. The defect inspecting apparatus 100 is then repaired in step S170.

A confirmation of the operation state of the defect inspecting apparatus 100 may be performed at random. Alternatively, the confirmation of the operation state of the defect inspecting apparatus 100 may be performed by periods. As one example, after about hundred wafers W are inspected the confirmation of the operation state of the defect inspecting apparatus 100 may be performed. As another example, the confirmation of the operation state of the defect inspecting apparatus 100 may be performed at about twelve hour intervals. As still another example, the confirmation of the operations state of the defect inspecting apparatus may be performed on a predetermined time.

As described above, after the operation state of the defect inspecting apparatus 100 is confirmed, the target defects on the wafer W is inspected. Thus, a result of the inspection of the wafer W may have a relatively high reliability. As a result, states of processes for manufacturing a semiconductor device using the wafer W may be easily determined to be normal or abnormal so that the semiconductor device manufactured by the processes may have superior characteristics.

According to the present invention, a standard sample is installed inside a defect inspecting apparatus so that an operation state of the defect inspecting apparatus may be rapidly and efficiently confirmed. Thus, target defects on a wafer may be efficiently inspected so that a reliability of a defect inspecting process using the defect inspecting apparatus may increase. In addition, it is possible to rapidly cope with mechanical troubles of the defect inspecting apparatus. Thus, losses of cost and time may be reduced. In addition, the operation state of the defect inspecting apparatus is automatically confirmed so that an efficiency of the defect inspecting process using the defect inspecting apparatus may be improved.

The foregoing is illustrative of the present invention and is not to be construed as limiting thereof. Although a few embodiments of this invention have been described, those skilled in the art will readily appreciate that many modifications are possible in the embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method of inspecting target defects on a wafer, the method comprising:

introducing the wafer into a defect inspecting apparatus;

operating the defect inspecting apparatus to obtain first information concerning standard defects on a standard sample;

comparing the first information with predetermined standard information to determine whether an operation state of the defect inspecting apparatus is normal or abnormal, the predetermined standard information being previously obtained; and determining whether or not to inspect the target defects on the wafer according to the operation state determined by comparing the first information with the predetermined standard information.

2. The method of claim 1, wherein the standard information concerns the standard defects on the standard sample.

3. The method of claim 1, wherein comparing the first information with the predetermined standard information comprises:

obtaining a first number of the standard defects from the first information;

calculating a difference between the first number of the standard defects and a second number of the standard defects, the second number of the standard defects being obtained from the standard information; and determining whether the operation state of the defect inspecting apparatus is normal or abnormal according to the difference.

4. The method of claim 3, wherein the first information includes a reflection signal resulting from light reflected from the standard sample; and wherein the difference is calculated by counting peaks of the reflection signal.

5. The method of claim 1, wherein obtaining the first information comprises:

scanning the standard sample with an incident light; and measuring light reflected from the standard sample.

6. The method of claim 5, wherein operating the defect inspecting apparatus comprises:

obtaining a first signal to noise ratio from the first information;

calculating a difference between the first signal to noise ratio and a second signal to noise ratio obtained from the standard information; and determining whether the operation state of the defect inspecting apparatus is normal or abnormal according to the difference.

7. The method of claim 6, wherein the first signal to noise ratio concerns a defect of interest among the standard defects.

8. The method of claim 1, wherein the operation state of the defect inspecting apparatus is determined to be either normal or abnormal by comparing the first information and the standard information.

9. The method of claim 1, wherein inspecting the target defects comprises:

scanning the wafer with incident light;

measuring reflected light from the wafer; and obtaining second information concerning the target defects on the wafer from the reflected light.

10. The method of claim 1, wherein the standard defect includes a polystyrene sphere latex particle.

11. A defect inspecting apparatus comprising:

a first support unit to support a standard sample;

a second support unit to support a wafer, the second support unit being adjacent to the first support unit;

a light source to irradiate an incident light onto either the standard sample or the wafer;

a light receiving part to collect first reflected light and second reflected light reflected from the standard sample and the wafer, respectively;

a detection part to detect standard defects on the standard sample and target defects on the wafer by using the first reflection light and the second reflection light, respectively;

a comparing part to compare first information and standard information to confirm a reliability of a target defect inspecting step that detects the target defects on the wafer, the first information concerning the standard defects, the first information resulting from the first reflected light, the standard information being previously obtained from the standard defects on the standard sample; and a determination portion determining whether the target defect inspecting step is allowed to be performed or not.

12. The defect inspecting apparatus of claim 11, wherein the standard sample includes standard sample units having different standard defects.

13. The defect inspecting apparatus of claim 11, wherein the first support unit and the second support unit are integral.

14. The defect inspecting apparatus of claim 13, wherein the standard sample is positioned adjacent to the wafer.

15. The defect inspecting apparatus of claim 11, further comprising:

a first drive unit to horizontally move the first support unit; and a second drive unit to horizontally move the second support unit.

16. The defect inspecting apparatus of claim 11, wherein the detection part includes a measurement module to count first intensity peaks of the first reflected light and second intensity peaks of the second reflected light to measure the number of the standard defects and the number of the target defects, respectively, wherein the first and second intensity peaks have a magnitude above a predetermined level.

17. The defect inspecting apparatus of claim 11, wherein the comparing part includes a calculation module to calculate a difference between a number of the standard defects obtained from the first information and a standard number of the standard defects obtained from the standard information, the calculation module to determine, responsive to the calculated difference, whether the defect inspecting apparatus is operating normally or not.

18. The defect inspecting apparatus of claim 11, wherein the comparing part is adapted to compare a first signal to noise ratio obtained from the first information with a standard signal to noise ratio obtained from the standard information to determine whether the defect inspecting apparatus is operating normally or not.

19. The defect inspecting apparatus of claim 11, further comprising a memory part to store the standard information.

20. The defect inspecting apparatus of claim 11, wherein the light source and the light receiving part are substantially in parallel with each other in vertical directions, the light source vertically irradiating the incident light, and the first and second reflected lights being vertically incident onto the light receiving part.

21. The defect inspecting apparatus of claim 11, wherein the incident light is divided into two separate light beams, one light beam incident on the wafer, and the other light beam incident on the standard sample.

* * * * *

UNITED STATES PATENT AND TRADEMARK OFFICE
CERTIFICATE OF CORRECTION

PATENT NO. : 7,426,031 B2  Page 1 of 1
APPLICATION NO. : 11/461726
DATED : September 16, 2008
INVENTOR(S) : Moon-Kyung Kim et al.

It is certified that error appears in the above-identified patent and that said Letters Patent is hereby corrected as shown below:

Column 1, line 59, the word "S115" should read -- S15 --;
Column 1, line 66, the word "S118" should read -- S18 --;
Column 11, line 67, the word "10" should read -- 110 --;
Column 12, line 37, the word "front" should read -- from --;
Column 12, line 62, the word "13" should read -- ±3 --.

Signed and Sealed this

Seventeenth Day of February, 2009

JOHN DOLL
*Acting Director of the United States Patent and Trademark Office*